US009162056B2

(12) United States Patent
Pianca (10) Patent No.: US 9,162,056 B2
(45) Date of Patent: Oct. 20, 2015

(54) PADDLE LEAD WITH INDICIA AND RELATED METHODS OF USE (71) Applicant: BOSTON SCIENTIFIC NEUROMODULATION CORPORATION, Valencia, CA (US)

(72) Inventor: Anne Margaret Pianca, Santa Monica, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 242 days.

(21) Appl. No.: 13/661,918

(22) Filed: Oct. 26, 2012

(65) Prior Publication Data
US 2013/0110211 A1 May 2, 2013

Related U.S. Application Data (60) Provisional application No. 61/552,318, filed on Oct. 27, 2011.

(51) Int. Cl.
A61N 1/05 (2006.01)
A61B 6/00 (2006.01)
A61B 6/12 (2006.01)

(52) U.S. Cl.
CPC ............... *A61N 1/0553* (2013.01); *A61B 6/12* (2013.01); *A61B 6/487* (2013.01); *A61N 1/0551* (2013.01)

(58) Field of Classification Search
CPC ............. A61B 19/54; A61B 2019/542; A61B 2019/5466; A61B 6/12; A61N 1/0553
USPC .......................................................... 607/117
See application file for complete search history.

(56) References Cited

U.S. PATENT DOCUMENTS

| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 2004/0260310 A1* | 12/2004 | Harris ........................... 606/117 |

(Continued)

OTHER PUBLICATIONS

International Application No. PCT/US2012/062162, International Search Report and Written Opinion mailed Jan. 16, 2013.

*Primary Examiner* — Michael Kahelin
*Assistant Examiner* — Minh Duc Pham
(74) *Attorney, Agent, or Firm* — Lowe Graham Jones PLLC; Bruce E. Black (57) ABSTRACT An implantable paddle lead includes a paddle body, configured and arranged for implantation in a patient's body, having a first face and a second face opposing the first face. The paddle lead also includes a plurality of electrodes disposed on the paddle body and configured and arranged for stimulating patient tissue adjacent the paddle body. The paddle lead further includes at least one indicium, independent of the plurality of electrodes, disposed on, or formed by, the paddle body. The at least one indicium is configured and arranged such that, when the paddle body is inserted within the patient's body and viewed under fluoroscopy, the at least one indicium identifies a facing orientation of the paddle body within the patient's body.

19 Claims, 7 Drawing Sheets

(56) References Cited

U.S. PATENT DOCUMENTS

| | | |
|---|---|---|
| 2005/0165465 A1 | 7/2005 | Pianca et al. |
| 2007/0021811 A1 | 1/2007 | D'Aquanni et al. |
| 2007/0150036 A1 | 6/2007 | Anderson |
| 2007/0203539 A1 | 8/2007 | Stone et al. |
| 2008/0132933 A1* | 6/2008 | Gerber ............... 606/191 |
| 2009/0054936 A1 | 2/2009 | Eggen et al. |
| 2009/0204192 A1* | 8/2009 | Carlton et al. ............ 607/116 |
| 2009/0270957 A1 | 10/2009 | Pianca et al. |
| 2010/0057179 A1 | 3/2010 | Storey |
| 2012/0083856 A1* | 4/2012 | Thacker et al. ............ 607/46 |
| 2013/0013039 A1* | 1/2013 | Daglow et al. ............ 607/116 |

* cited by examiner

PADDLE LEAD WITH INDICIA AND RELATED METHODS OF USE

CROSS-REFERENCE TO RELATED APPLICATIONS

This application claims the benefit under 35 U.S.C. §119 (e) of U.S. Provisional Patent Application Ser. No. 61/552,318 filed on Oct. 27, 2011, which is incorporated herein by reference.

FIELD OF THE INVENTION

The present invention is directed to the area of implantable electrical stimulation systems and methods of making and using the systems. The present invention is also directed to implantable electrical stimulation leads having indicia for assisting implantation.

BACKGROUND

Implantable electrical stimulation systems have proven therapeutic in a variety of diseases and disorders. For example, spinal cord stimulation systems may be implanted in the spinal cord to treat chronic pain syndromes and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue including subcutaneous nerves such as the occipital nerve.

In general, a stimulator includes a control module (with a pulse generator), one or more leads, a paddle body connected to the distal end of the lead(s), and an array of stimulator electrodes mounted on the paddle body. The stimulator electrodes are placed in contact with or near the nerves, muscles, or other tissue to be stimulated. The pulse generator in the control module generates electrical pulses that are delivered through the electrodes to body tissue.

BRIEF SUMMARY

One embodiment is an implantable paddle lead. The paddle lead includes a paddle body, configured and arranged for implantation in a patient's body, having a first face and a second face opposing the first face. The paddle lead also includes a plurality of electrodes disposed on the paddle body and configured and arranged for stimulating patient tissue adjacent the paddle body. The paddle lead further includes at least one indicium, independent of the plurality of electrodes, disposed on, or formed by, the paddle body. The at least one indicium is configured and arranged such that, when the paddle body is inserted within the patient's body and viewed under fluoroscopy, the at least one indicium identifies a facing orientation of the paddle body within the patient's body.

In another embodiment, a stimulation system includes a paddle adapted for implantation in a patient's body, the paddle having a first face, a second face, and one or more electrodes disposed on the first face. The stimulation system also includes a control module connectable to the proximal end of the paddle using at least one lead. The stimulation system further includes an indicium, including a radiopaque material, being disposed on at least one of the first face or second face of the paddle. The indicium is configured and arranged so that a fluoroscopic image of the paddle, when implanted in a patient, identifies a facing orientation of the first face of the paddle within the patient.

In yet another embodiment, a method for implanting a paddle lead includes advancing the paddle lead, as described above, into a patient's body. A fluoroscopic image of the paddle lead is captured. A facing orientation of the paddle lead is identified by observing the at least one indicium on the fluoroscopic image.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

Corresponding reference characters indicate corresponding components throughout the several views of the drawings.

DETAILED DESCRIPTION

Embodiments of the present disclosure relate to implantable electrical stimulation systems and related methods of use. The stimulation system includes a paddle body, disposed with one or more electrodes. A lead connects the proximal end of the paddle body to a stimulator. The stimulation system is implanted in a patient's body for providing stimulation to one or more body parts.

To provide effective stimulation, the electrodes should face the desired body part. For example, in spinal cord stimulation, the electrodes typically face the dura layer. During implantation of the paddle body, however, the paddle body may twist or turn such that it may not be deployed in the desired orientation (e.g., toward the dura).

Conventionally, confirming the deployed orientation of the paddle body can be time consuming and ineffective. A surgeon may take several fluoroscopic images of the paddle body to identify whether the electrodes are facing in the desired orientation. The fluoroscopic images may not identify the orientation of the electrodes unambiguously. In such situations, the inappropriately placed paddle may remain deployed within the patient, resulting in ineffective stimulation. Subsequent surgery may be required to re-implant the stimulation system in the desired direction.

To facilitate determination of the facing orientation of a paddle body, the paddle body can incorporate one or more indicium that help in determining whether the paddle body is disposed in the correct orientation. The term "facing orientation" of a paddle body refers to the direction that one of the major surfaces (e.g., the first surface or the second surface) of the paddle body is facing. In at least some embodiments, the objective of inclusion of the one or more indicium is to determine whether a major surface of the paddle body containing electrodes is facing toward tissue to be stimulated or away from that tissue. The paddle body is often quite small and it may be difficult to determine which major surface is facing the tissue to be stimulated when the paddle body is implanted into the patient's body. For purposes of definition, a "facing" direction may be selected as the direction perpendicular to the major surface.

Various alternatives of the directional indicia may be contemplated. In general, the one or more indicium can be formed by, for example, embedding or coating radio-opaque markings on the paddle body such that that a fluoroscopic image of the implanted paddle body identifies the facing orientation of the implanted paddle body. For example, indicia may include, for example, fluoroscopically viewable material in the form of symbols which are visually different depending on the facing orientation of the paddle. By knowing the expected image of the indicium under fluoroscopy, the orientation of the paddle may be determined. Alternatively, the fluoroscopic image of the one or more indicium may itself be indicative of paddle's orientation. The indicia may include symbols, words, or any kind of marking. Alternatively, the one or more indicium may include cutout sections of the paddle body.

Suitable implantable electrical stimulation systems include, but are not limited to, an electrode ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; and U.S. Patent Application Publication Nos. 2005/0165465 and 2007/0150036, all of which are incorporated by reference.

In the following sections, embodiments of the present disclosure will be described with reference to spinal cord stimulation. It will be understood that this choice is merely exemplary and that the device may be utilized in any other organ, such as the brain, urinary system, or any other organ or tissue that can be stimulated.

Figure 1:
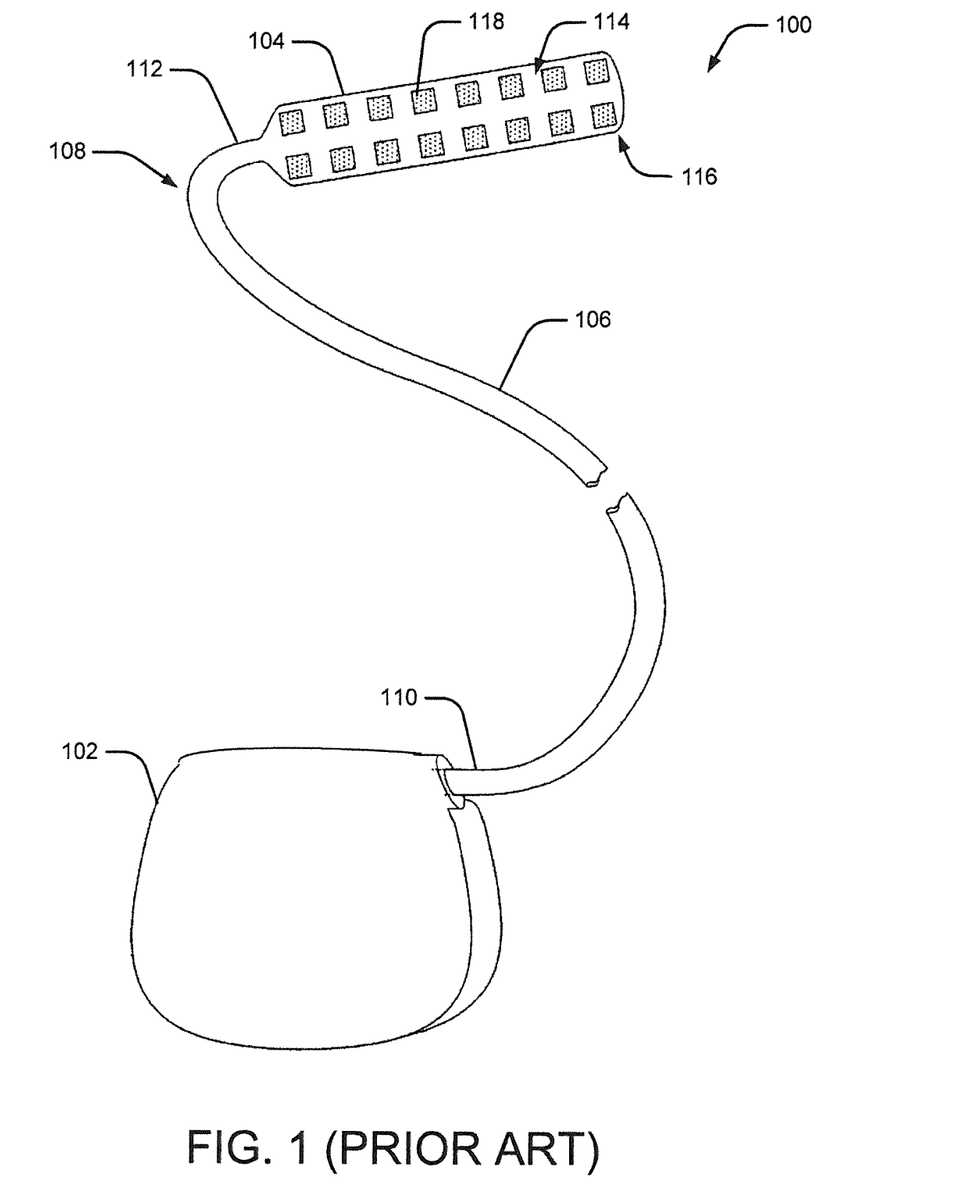
FIG. 1 is a perspective view of a stimulation system, according to the invention.

FIG. 1 illustrates one embodiment of a stimulation system 100. Stimulation system 100 includes a control module 102, such as a stimulator or pulse generator, a paddle body 104, and at least one lead body 106 coupling control module 102 to paddle body 104. One or more components of stimulation system 100 are typically implanted into a patient's body. The stimulation system can be used for a variety of applications including, but not limited to, brain stimulation, neural stimulation, spinal cord stimulation, muscle stimulation, and the like.

Paddle body 104 along with lead body 106 forms a paddle lead 108. The paddle body 104 and lead body 106 may be a unitary structure or these two components may be formed as separate structures that are permanently or detachably coupled. Lead body 106 may be, for example, a round or tubular lead body having a proximal end 110 and a distal end 112 with at least one electrical conductor (not shown) extending between the proximal end 110 and distal end 112. The proximal end 110 of the lead body includes an array of terminal contacts (not shown) which are coupled to the electrical conductors and, through the conductors, to the electrodes described below.

Paddle body 104 is, in at least some embodiments, a generally flat body provided on the distal end of lead 106. In at least some embodiments, the paddle body has two major surfaces defining, respectively, a first face 114 and a second face 116. Typically, the first and second faces are on opposite sides of the paddle body. The first face 114 includes an array of electrodes 118, which are in electrical communication with the electrical conductor. In some embodiments, the second face 116 may also include one or more electrodes.

Electrodes 118 can be formed using any conductive, biocompatible material. Examples of suitable materials include metals, alloys, conductive polymers, conductive carbon, or combinations thereof. The number of electrodes in the array may vary. For example, there can be one, two, four, eight, ten, twelve, sixteen, or more electrodes. Further, the electrodes may be disposed on one or both faces of the paddle body. In at least some embodiments, the electrodes are arranged in an array of one or more columns and one or more rows. Alternatively, electrodes may be arranged in any other regular or irregular arrangement on the paddle body.

Electrical current is provided through one or more of the electrodes 118 to stimulate nerve fibers, muscle fibers, or other body tissues near the stimulation system. In one embodiment, a processor, within the control module 102, is included to control the timing and electrical characteristics of the stimulation system. For example, the processor can, if desired, control one or more of the amplitude, pulse width (duration), frequency, and polarity of the pulses. In addition, the processor can select which electrodes can be used to provide stimulation.

It will be understood that stimulation system 100 can include more, fewer, or different components and can have a variety of different configurations known to those skilled in the art. Further, paddle body 104 may be elliptical or tubular in shape.

For spinal cord stimulation, paddle lead 108 is implanted within the spinal column of a patient. That procedure, known as laminectomy, involves removal of the laminar vertebral tissue to allow access to the dura layer, followed by implementation of paddle lead 108. Alternatively, paddle lead 108 may be introduced percutaneously into the epidural space through a Tuohy-like needle, which passes through the skin between the desired vertebrae and into the epidural space above the dura layer. In general, the first face 114 having electrodes (hereafter, referred "first face 114") faces the dura layer and the second face 116 (hereafter, referred "second face 116") faces the spinal cord. During this procedure, however, paddle body 104 may twist or flip such that first face 114 may face the spinal cord. If paddle body 104 is inappropriately deployed, it may provide ineffective or less effective stimulation.

Figure 2A:
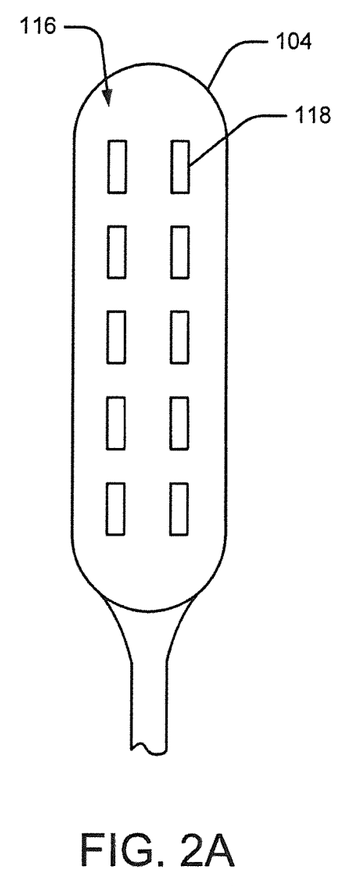
FIGS. 2A and 2B illustrate fluoroscopic images of opposing first and second sides of an embodiment of a conventional paddle lead.
Figure 2B:
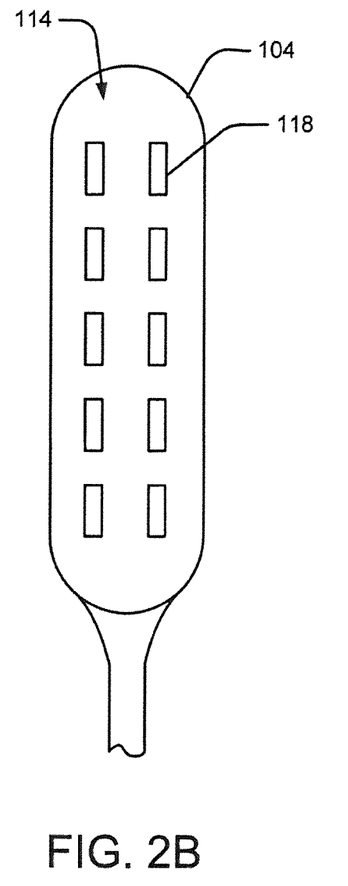

During or after implantation, it is desirable to confirm that electrodes 118 are correctly oriented in the right facing direction. For example, the active surface of electrodes 118 should face the dura mater and not the bone structure. In general, as electrodes are made of a material that can be imaged through the surrounding tissue, different imaging techniques, such as fluoroscopy, x-ray imaging, CT, or magnetic resonance, may be implemented to confirm the orientation of the paddle body 104. Unfortunately, the conventional symmetric paddle designs may not assist in ascertaining a correct facing orientation. For example, FIGS. 2A and 2B depict fluoroscopic images of a conventional paddle body 104 in the correct (FIG. 2A) and incorrect (FIG. 2B) facing orientations, respectively. As it is evident, however, both images are identical, making an unambiguous identification of the facing orientation of the paddle body difficult, if not impossible. Consequently, a surgeon may require more surgical time in the operating room, to ensure correct placement of paddle body 104.

To facilitate determination of facing orientation using imaging, a paddle lead may employ one or more directional markings. The directional markings may include one or more indicium made from fluoroscopically viewable radio-opaque material. In general, indicia include symbols or signs embedded on the paddle body 104 such that a surgeon may distinguish the first and second faces 114, 116. By comparing the orientation, design, or shape of the indicium or indicia in a fluoroscopic image with the expected indicium or indicia, a surgeon can identify a correct orientation of a paddle body. Alternatively or additionally, the paddle image, having the indicia, may itself be indicative of the current orientation. Although fluoroscopy is used as an example of an imaging technique, it will be understood that other imaging techniques, for example, magnetic resonance imaging, may be used and that the indicium or indicia would be selected and formed to be observable under that imaging technique. In some embodiments, the indicium or indicia would be selected and formed to be observable using multiple imaging techniques.

The indicium or indicia may be positioned at any desired location on the paddle. For example, self-indicative indicia, such as alphanumeric characters, arrows, pointers, and the like, may be placed anywhere on the paddle to indicate orientation. FIGS. 3A, 3B, 4A, 4B, 5A, and 5B illustrate examples of such indicia.

Figure 3A:
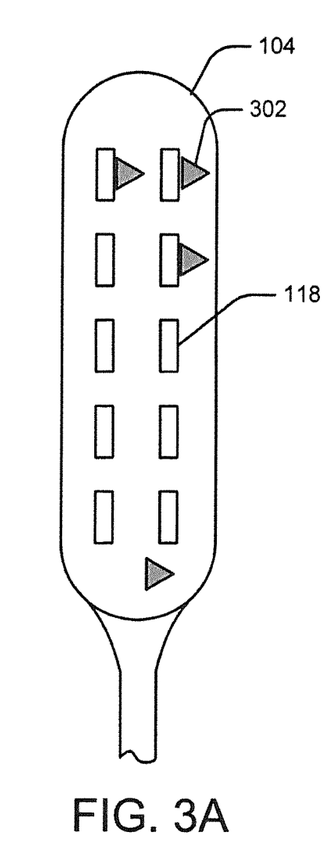
FIGS. 3A and 3B are top and bottom views of one embodiment of a paddle body with indicia disposed thereon, according to the invention.
Figure 3B:
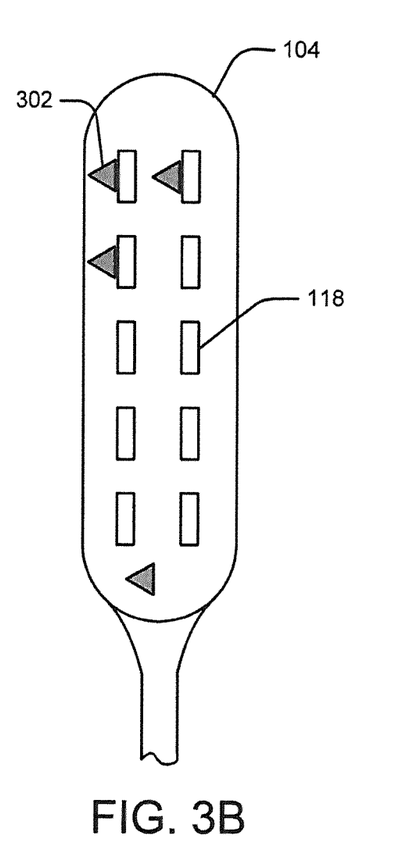

FIGS. 3A and 3B each depict an image of paddle body 104, indicating correct and incorrect facing orientations in the epidural space, respectively. The paddle body 104 includes one or more 302, for example, triangles or chevrons 302, affixed to first face 114 or second face 116. As shown in the specific example of FIGS. 3A and 3B, four symbols 302 are embedded during manufacture, positioned on the paddle body or on the electrode itself. Symbols 302 may be made of any radiopaque biocompatible material, for example, a metal such as platinum, platinum iridium, stainless steel, titanium, or any combination thereof. In an alternate embodiment, symbols 302 may be made of a polymer carrying a radiopaque material, such as silicone embedded with barium sulphate or titanium dioxide. Further, these symbols may be molded with the paddle 104 during manufacture, or later attached to the surface of the paddle 104 using any known attachment mechanism (e.g., an adhesive or the like).

The orientation of symbols 302 in a fluoroscopic image identifies the facing orientation of the paddle body 104. In general, symbols 302 may be positioned to point towards a pre-determined direction. Under fluoroscopy, symbols 302 clearly indicate the facing orientation of an implanted paddle body 104. In addition, the conductor wires in the lead (not shown) that are typically attached to the paddle body may assist in identifying which face of the paddle body is turned toward the target stimulation tissue.

FIG. 3A depicts a fluoroscopic image of paddle 104 indicating a correct facing orientation, where the first face 114 is facing the dura layer. As shown, symbols 302 are pointing towards the right. A flipped paddle will display a mirror image of FIG. 3A, as shown in FIG. 3B. Those skilled in the art will understand that the terms "left" and "right" may be interchangeably used throughout the present disclosure. By knowing the expected orientation or direction of indicia in a fluoroscopic image, a surgeon can decide whether paddle 104 has the desired facing orientation. A misplaced paddle may need to be flipped or reinserted in the correct facing orientation.

Figure 4A:
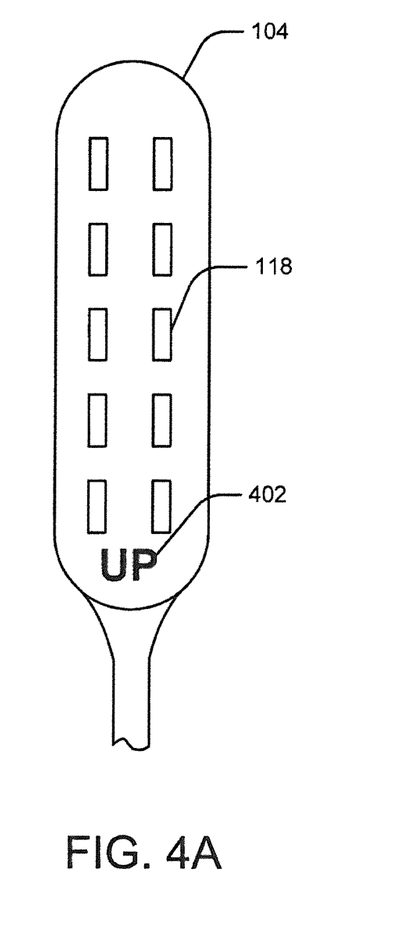
FIGS. 4A and 4B are top and bottom views of a second embodiment of a paddle body with indicia disposed thereon, according to the invention.
Figure 4B:
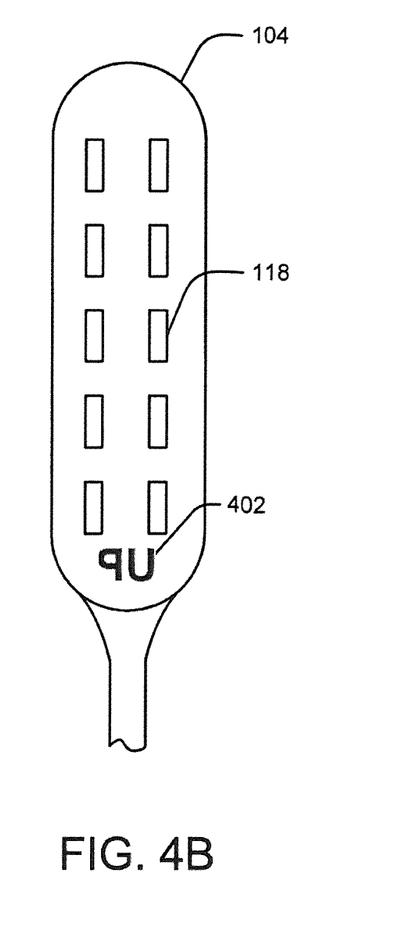

FIGS. 4A and 4B illustrate another embodiment of a paddle body with indicia. Here, instead of symbols, the indicia take the form of alphanumeric characters or indicators such that a desired orientation may fluoroscopically display readable markings. It should be understood that such indicia may be provided at any desired position on either face of the paddle. In the illustrated embodiment, the word "UP" at location 402, in FIG. 4A, is presented when the paddle body is in the correct facing orientation. FIG. 4B depicts the image that would be obtained if the paddle body were in the wrong facing orientation as indicated by the mirror image of the word at location 402. In some embodiments, such as that illustrated in FIGS. 4A and 4B, the indicium or indicia are "self-indicative" meaning that a practitioner would know the proper facing orientation of the indicium or indicia based simply on observation without any further instructions. This is in contrast to the indicia illustrated in FIGS. 3A and 3B which require that the practitioner also know whether the arrow-like indicia should point right or left. Adding self-indicative indicia sidesteps any requirement to inform the surgeon of the expected image in advance. The surgeon will be able to determine paddle's orientation unambiguously by simply viewing its fluoroscopic image. It should be understood that any desired character or indicators may be used such that the desired and mirror images of the markings may itself identify whether paddle 104 is oriented in the right direction.

Figure 5A:
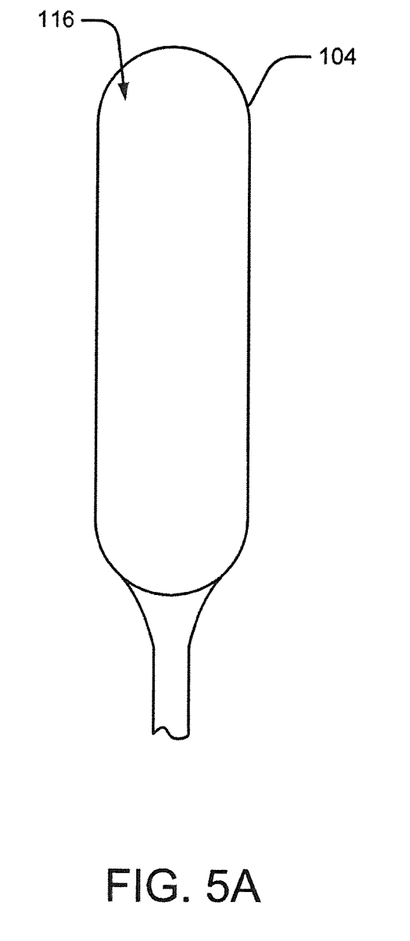
FIGS. 5A and 5B are top and bottom views of a third embodiment of a paddle body with indicia disposed thereon, according to the invention.
Figure 5B:
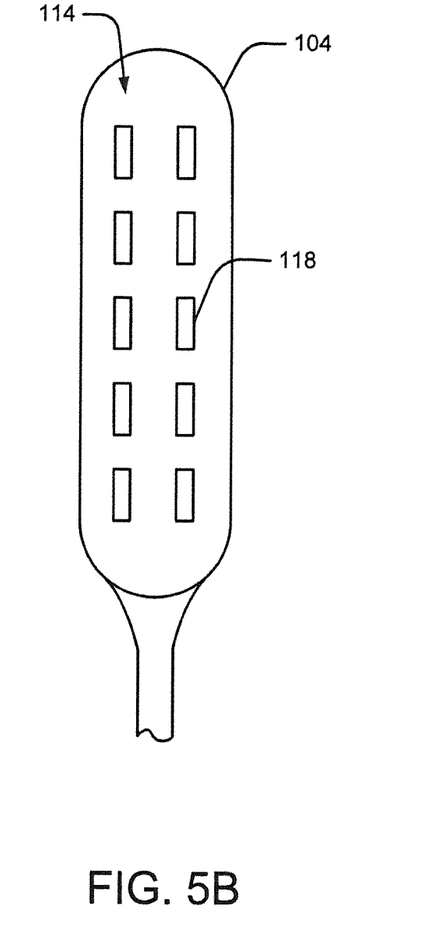

In an alternate embodiment, a large portion (for example, at least 25%, 33%, 50%, 66%, 75%, 80%, 90%, or 95%), or the complete, second face 116, which faces towards the bone structure in spinal cord stimulation, may be covered with a radio-opaque material. A fluoroscopic image of second face 116 hides at least some, or all, of the electrodes 118 disposed on first face 114, as shown in FIG. 5A, when the paddle body 104 is in the correct facing orientation. FIG. 5B illustrates a fluoroscopic image depicting the electrodes when the paddle body 104 is in the incorrect facing position. It will be understood that, to be effective, the electrodes 118 must be fluoroscopically distinguishable from the covered portion of the second face. This may be accomplished, for example, by using different materials for the electrodes and the covering on the portion of the second face. Using indicia in the form of coverings, either face of paddle 104 can be discerned conveniently by capturing a fluoroscopic image of the deployed paddle 104. Also, by simply looking at the fluoroscopic image a surgeon can confirm whether the paddle has flipped during insertion.

Some indicium or indicia may not be self-indicative. For example, an indicium or indicia can be positioned asymmetrically along the width of paddle, such as on either side of the paddle's longitudinal axis (shown as dotted line in FIGS. 6A and 6B). The fluoroscopic orientation of the indicium or indicia with respect to the longitudinal axis determines whether paddle body 104 has flipped during deployment so that the paddle body no longer has the desired facing orientation.

Figure 6A:
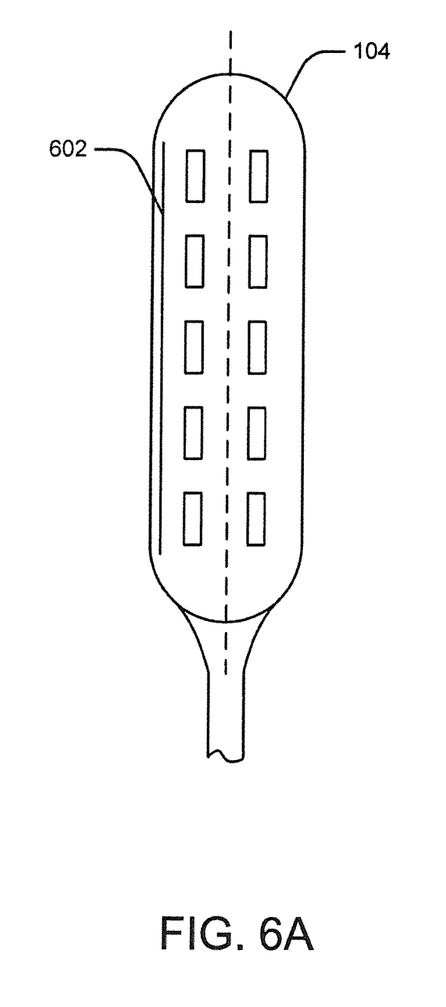
FIGS. 6A and 6B are top and bottom views of a fourth embodiment of a paddle body with indicia disposed thereon, according to the invention.
Figure 6B:
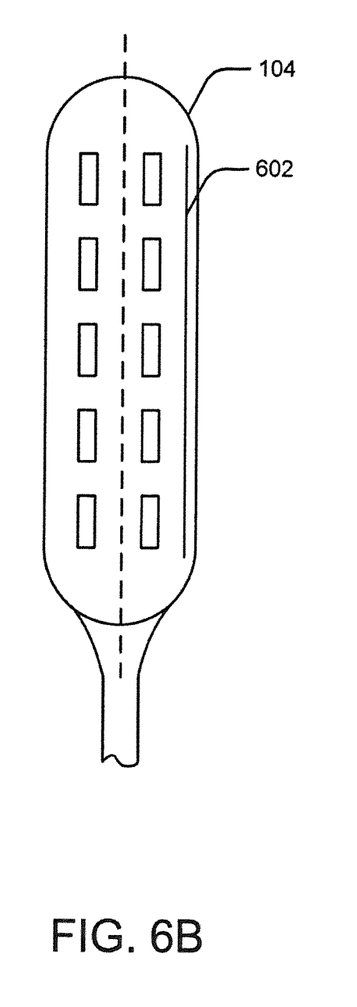

FIGS. 6A and 6B depict a radiopaque vertical line 602 disposed parallel to the longitudinal axis. This line appearing on the desired side of the paddle body 104 in a fluoroscopic image indicates a correct facing orientation. FIG. 6A depicts the line 602 appearing on the right side of paddle indicating to a practitioner that the first face 114 (including electrodes) is facing the dura layer. The opposite result, with line 602 on the left, shown in FIG. 6B, indicates an incorrect facing orientation. Line 602 may be a simple radiopaque metal wire or an insulating wire embedded within, or disposed on, the paddle during manufacture.

Figure 7A:
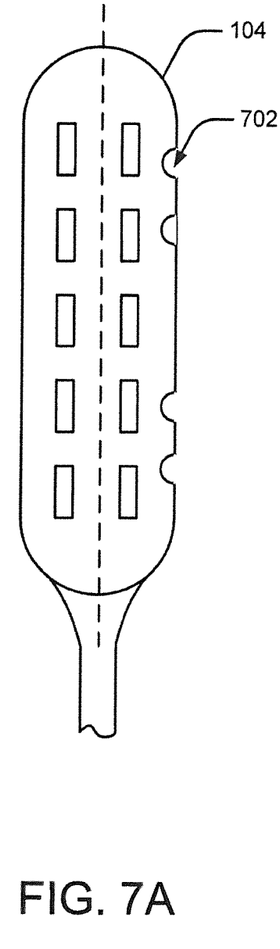
FIGS. 7A and 7B are top and bottom views of one embodiment of a paddle body with indicia in the form of cutouts therein, according to the invention.
Figure 7B:
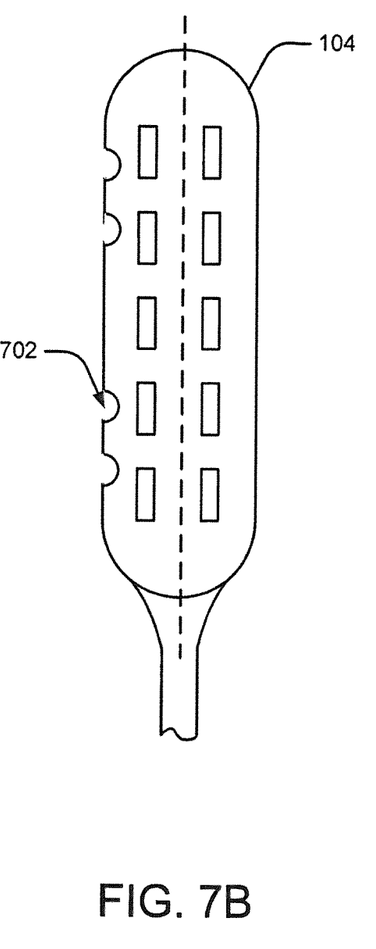

Instead of, or in addition to, radiopaque indicia, paddle body 104 may include geometrical structures or designs that are visible on a fluoroscopic image. FIGS. 7A and 7B illustrate an embodiment of indicia that are cutout sections 702 along the edges of paddle body 104. As shown, semi-circular cutouts are created asymmetrically along the edges of the paddle body. In the illustrated embodiment, a fluoroscopic image depicting cutouts 702 on the right side of the paddle, FIG. 7A, indicates the correct facing orientation. Cutouts, however, on opposite side (the left side) indicates the incorrect facing orientation. It should be understood that cutouts 702 may be created on any desired side or location on paddle body 104 and may be provided on both opposing edges of the paddle body (although typically in different patterns). Further, the number, size, and shape of the cutouts 702 may selected individually and size and shape of the cutouts may be uniform or non-uniform.

It will be understood that any combination of the indicia discussed above can be used. For example, paddle body 104 may include symbols 302 and line 602 to distinguish between the two faces 114, 116. Alternatively, first face 114 may include word 402 while the second face 116 may be coated with a radiopaque material. In this embodiment, a fluoroscopic image displaying a readable word ("UP") identifies first face 114 pointing towards the bone structure, indicating an incorrect facing orientation.

In at least some embodiments, a practitioner can discern the first and second faces 114, 116 of paddle 104 in a cost-effective and efficient manner. For example, in some embodiments, before implanting the complete stimulation system, the paddle body 104 or the paddle along with the lead may be inserted within a patient's body. Once the paddle body 104 is deployed in epidural space, a fluoroscopic image of paddle body 104 is obtained. In some embodiments, the fluoroscopic image may itself be indicative of orientation of the paddle body 104. For example, incomprehensible or unreadable characters or indicators (discussed in FIGS. 4 and 5) on the image denote incorrectly oriented paddle 104.

In other embodiments, a practitioner may need to have knowledge of the expected correct image to decide whether the first face 114 is facing the dura layer. To educate the practitioner, a manual or other instructional material specifying the desired images for appropriate deployment may be provided. In an embodiment, the control module 102 may also include a display screen, decal, or other indicia presenting the expected fluoroscopic image for a correctly oriented paddle body 104.

If the indicia discussed above identify paddle body 104 as being incorrectly oriented, then paddle body 104 may be retrieved and reinserted in the desired directions. Subsequently, another image of the deployed paddle can determine whether the re-insertion was successful. On confirming the desired orientation of the paddle body 104, one or more components of the stimulation system 100 may be implanted within the body to perform the desired procedure. As a result, utilizing indicia, the embodiments of the present disclosure distinguish either face of the paddle body to determine whether the paddle lead 108 is deployed appropriately within a patient's body.

Embodiments of the present disclosure may be used in any medical or non-medical procedure, including any medical procedure where one or more body part requires electrical stimulation. In addition, at least certain aspects of the aforementioned embodiments may be combined with other aspects of the embodiments, or removed, without departing from the scope of the preset disclosure.

While the present disclosure has been described by means of specific embodiments and applications thereof, numerous modifications and variations could be made thereto by those skilled in the art without departing from the scope of the present disclosure set forth in the claims.

What is claimed is:

1. An implantable paddle lead, comprising:
    a paddle body, configured and arranged for implantation in a patient's body, having a first face and a second face opposing the first face;
    a plurality of electrodes disposed on the paddle body and configured and arranged for stimulating patient tissue adjacent the paddle body; and
    at least one indicium, independent of the plurality of electrodes, disposed on the paddle body, wherein the at least one indicium comprises a radiopaque material and is configured and arranged such that, when the paddle body is inserted within the patient's body and viewed under fluoroscopy, the at least one indicium identifies a facing orientation of the paddle body within the patient's body, wherein at least 33% of the second face is coated with the at least one indicium including a portion of the second face opposite one or more of the plurality of electrodes to hide the one or more of the plurality of electrodes in a fluoroscopic image if the paddle body is in a correct facing orientation, wherein the at least one indicium is fluoroscopically distinguishable from the plurality of electrodes.

2. The paddle lead of claim 1, wherein at least 90% of the second face is coated with the at least one indicium.

3. A stimulation system, comprising:
    the paddle lead of claim 1; and
    a control module coupleable to the paddle lead.

4. A method for implanting a paddle lead, the method comprising:
    advancing the paddle lead of claim 1 into a patient's body;
    capturing a fluoroscopic image of the paddle lead; and
    identifying a facing orientation of the paddle lead by observing the at least one indicium on the fluoroscopic image.

5. The method of claim 4, wherein identifying a facing orientation of the paddle lead comprises comparing the fluoroscopic image with a predetermined desired image.

6. The method of claim 4, further comprising revising the facing orientation of the paddle lead upon a determination that the paddle lead is implanted with an incorrect facing orientation.

7. The method of claim 6, wherein revising the facing orientation of the paddle lead comprises explanting the paddle lead and then reimplanting the paddle lead.

8. The method of claim 7, further comprising capturing a fluoroscopic image of the reimplanted paddle lead; and identifying a facing orientation of the reimplanted paddle lead by observing the at least one indicium on the fluoroscopic image.

9. The method of claim 4, further comprising coupling the paddle lead to an implantable control module.

10. The paddle lead of claim 1, wherein at least 50% of the second face is coated with the at least one indicium.

11. The paddle lead of claim 1, wherein all of the second face is coated with the at least one indicium.

12. The paddle lead of claim 1, wherein the at least one indicium is configured and arranged to hide all of the plurality of electrodes from fluoroscopic observation when the paddle body is correctly inserted within the patient's body.

13. The paddle lead of claim 1, wherein the at least one indicium is disposed over an entire portion of the second face that is opposite the plurality of electrodes.

14. An implantable paddle lead, comprising:
a paddle body, configured and arranged for implantation in a patient's body, having a first face and a second face opposing the first face;
a plurality of electrodes disposed on the paddle body and configured and arranged for stimulating patient tissue adjacent the paddle body; and
at least one indicium, independent of the plurality of electrodes, disposed on the paddle body, wherein the at least one indicium comprises a radiopaque material and is configured and arranged such that, when the paddle body is inserted within the patient's body and viewed under fluoroscopy, the at least one indicium identifies a facing orientation of the paddle body within the patient's body, wherein the at least one indicium comprises a plurality of cutout sections formed by at least a portion of the paddle body, wherein the cutout sections are all disposed on a same side of the paddle body.

15. The paddle lead of claim 14, wherein the at least one indicium further comprises at least one symbol.

16. The paddle lead of claim 14, wherein the at least one indicium further comprises at least one alphanumeric character.

17. A stimulation system, comprising:
the paddle lead of claim 14; and
a control module coupleable to the paddle lead.

18. A method for implanting a paddle lead, the method comprising:
advancing the paddle lead of claim 14 into a patient's body;
capturing a fluoroscopic image of the paddle lead; and
identifying a facing orientation of the paddle lead by observing the at least one indicium on the fluoroscopic image.

19. The paddle lead of claim 14, wherein the cutout sections are disposed in an asymmetric pattern along the same side of the paddle body.

* * * * *